United States Patent [19]

Liu

[11] Patent Number: 5,237,876
[45] Date of Patent: Aug. 24, 1993

[54] APPARATUS FOR TENSILE TESTING PLATE-TYPE CERAMIC SPECIMENS

[75] Inventor: Kenneth C. Liu, Oak Ridge, Tenn.

[73] Assignee: Martin Marietta Energy Systems, Inc., Oak Ridge, Tenn.

[21] Appl. No.: 922,451

[22] Filed: Jul. 29, 1992

[51] Int. Cl.$^5$ ............................................. G01N 3/08
[52] U.S. Cl. ..................................................... 73/831
[58] Field of Search .................. 73/826, 827, 831–834, 73/837, 856, 857, 860

[56] References Cited

U.S. PATENT DOCUMENTS

| | | | |
|---|---|---|---|
| 3,107,524 | 10/1963 | O'Connor | 73/860 |
| 3,802,255 | 4/1974 | Struthers et al. | 73/856 |
| 4,686,860 | 8/1987 | Liu . | |
| 4,845,997 | 7/1989 | Radin et al. | 73/831 |

OTHER PUBLICATIONS

"Towards Routine Tensile Testing" Tatsuki OHJI, Government Research Institution, Nagoya, Japan, Int. J. High Technology Ceramics, vol. 4, 1988.
"Tensile Testing of Ceramics", S. P. Sehadri et al, Journal of Americal Ceramic Society, vol. 70, Oct. 1987, pp. C-242 to C-244.

Primary Examiner—Robert Raevis
Attorney, Agent, or Firm—Earl L. Larcher; J. Donald Griffin; Harold W. Adams

[57] ABSTRACT

Apparatus for tensile testing plate-type ceramic specimens having dogbone- or T-shaped end sections without introducing bending stresses in the specimens during the application of a dynamic tensile loading on the specimens is described. A pair of elongated pull rods disposed in a side-by-side relationship are used to grip the shoulders on each T-shaped end section. The pull rods are pivotally attached to a piston-displaceable, disk-shaped member so as to be longitudinally movable with respect to one another effecting the self-alignment thereof with the shoulders on the T-shaped end sections of the specimen to compensate for shoulders being located in different longitudinal positions.

9 Claims, 2 Drawing Sheets

APPARATUS FOR TENSILE TESTING PLATE-TYPE CERAMIC SPECIMENS

This invention was made with the support of the United States Government under contract No. DE-AC05-84OR21 400 awarded by the U.S. Department of Energy. The United States Government has certain rights in this invention.

BACKGROUND OF THE INVENTION

The present invention relates generally to an apparatus for tensile testing flat or plate-type ceramic specimens to determine the strength properties of various ceramics, and more particularly to such apparatus incorporating a self-aligning pull rod system utilized for gripping such ceramic specimens during the tensile testing thereof so that no or essentially no bending stresses will be applied to the specimen during the testing thereof.

The determination of the mechanical properties of ceramic materials is becoming of increasing importance with the advert of recently developed ceramics which have been found to be useful as structural materials in many engineering applications such as fabrication of heat engines and gas turbines. Accuracy in the testing of the ceramic materials to determine the strength, especially the tensile strength, thereof is of considerable importance regarding the use of the ceramic materials in most engineering applications. In such tensile testing of ceramics, it is particularly critical to the accuracy of the test to apply the tensile loading on the ceramic specimen without introducing deleterious bending stresses in the specimen since non-uniformly applied loadings on the specimen can bias test results due to the random nature of process defect distribution pre-existing in the specimen coupled with the high sensitivity of fracture initiation characteristics inherent to brittle ceramic materials.

A recent development in tensile testing ceramic specimens is described in U.S. Pat. No. 4,686,860 which issued Aug. 18, 1987 in the name of Kenneth C. Liu, the inventor in the instant application. In this patent, a self-aligning multiple hydraulic piston assembly and specimen gripping arrangement is provided for applying tensile loadings on ceramic specimens of cylindrical configurations while transmitting little or no bending stresses to the ceramic specimens. However, while this patented development provides highly accurate tensile testing of cylindrical specimens, the tensile testing of flat or plate-type ceramic specimens, especially ceramic specimens having the so-called "dogbone" shape as defined by generally T-shaped end sections, without introducing undesirable bending stresses in test conditions has not yet been satisfactorily addressed. One of the principal problems encountered during the tensile testing of the flat ceramic specimens is that the tolerances used in the formation of the specimen by machining or any other technique are highly critical in order to assure that the no or essentially no bending stresses will be applied to the tensile specimen during the application of a tensile load thereon.

For example, a previous effort used for tensile testing dogbone-shaped, plate-type ceramic specimens involved the placement of clevis pins at each end of the specimen for assuring that the tensile loading applied through the clevis pins is directed along the longitudinal center of the specimen. This clevis pin fixture requires that holes be machined at precise locations in the opposite ends of the specimen for receiving the clevis pins which are used to attach the specimen to a tensile load applying mechanism. The provision of these holes in the ceramic specimen was found to be difficult to achieve, especially in a reproducible manner, for accurately aligning the specimen with respect to the direction of applied force.

Another effort previously used for tensile testing dogbone-shaped plate-type tensile specimens is described in a technical article entitled "Towards Routine Tensile Testing" by Tatsuki, OHJI, Government Research Institution, Nagoya, Japan, Int. J. High Technology Ceramics, Vol. No. 4, 1988. In this technical article the specimen-gripping pull rod mechanism utilizes pins which bear against the shoulders on the T-shaped ends of each specimen for holding the specimen in the pull rod. Each pull rod is provided with universal joints for load distribution purposes. The tensile specimens used in this specimen-gripping mechanism must be machined to precise and reproducible tolerances so as to be accurately tested without encountering deleterious bending stresses. However, such precise machining is of considerable expense and difficult to achieve, especially in a reproducible manner.

A further effort for tensile testing plate-type ceramic specimens is described in another technical article entitled, "Tensile Testing of Ceramics" by S. P. Sehadri et al, Journal of American Ceramic Society, Volume 70, Oct. 1987, pp. C-242 to C-244. In this article the tensile specimens are provided with wedge-shaped ends each of which is confined between two pin-mounted, flat-sided grip blocks which are rotatable about the pins by the wedge-shaped specimen to align the specimen in a plane parallel with the pull rod during the application of the tensile loading. While this fixture apparently obviates the requirement for precise machining of the specimens and minimizes bending stresses on the specimen during testing, the fixture requires the use of wedge-shaped specimens which require a configuration with a strict symmetry with respect to the loading axis rather than the more commonly used and easier formed dogbone-shaped plate-type specimens.

SUMMARY OF THE INVENTION

Accordingly, it is a principal aim or objective of the present invention to provide an apparatus for testing the strength characteristics of dogbone-shaped, plate-type ceramic tensile specimens without inducing undesirable bending stresses in the specimen during tensile testing thereof and without requiring that the tensile specimens be machined to rigid tolerances for accurately testing the specimen.

Another object of the present invention is to provide a pull rod assembly which grips the generally T-shaped ends of dogbone-shaped, flat or plate-type ceramic specimens in such a manner that the tensile loading on the specimen is always through the centerline of the tensile specimen.

A further object of the present invention is to provide a pull rod assembly having self-aligning features when employed in a multiple piston load applying mechanism as described in the aforementioned U.S. patent whereby accurate tensile tests can be performed on a dogbone-shaped, plate-type ceramic tensile specimen without imposing bending stresses thereon even when the load bearing shoulders on each end of the specimen are not in the same transverse or horizontal plane.

Generally, the apparatus of the present invention is utilized for gripping a plate-type ceramic tensile specimen having generally T-shaped end regions in a dynamic tension-tension fatigue testing mechanism comprising an annular housing having an elongated cavity therein, a plurality of hydraulic piston means supported by the housing in a circumferentially spaced array about a circumference of the cavity, and a piston displacing specimen supporting plate means overlying the piston means at one end of the elongated cavity. This apparatus for gripping the plate-type tensile specimen is self-aligning and comprises: a pair of elongated pull rod means having oppositely disposed first and second end regions; mounting means carried by the plate means for pivotally attaching the first end region of each of the pull rod means to a central region of the plate means for supporting the pull rod means in a side-by-side relationship within the cavity; recess means in the second end region of each of the pull rod means in adjacently disposed surface regions thereof and facing one another and with each recess means adapted to receive one side of the generally T-shaped end region of the plate-type tensile specimen; and load-bearing means positionable in each of the recess means and adapted to bear against a shoulder on each side of the generally T-shaped end region of the plate-type tensile specimen when a tensile loading is applied thereon. When the plate means is displaced by piston means the pull rods are movable with respect to one another as provided by a slight canting or "tipping" of the plate means for assuring that the loading applied on the tensile specimen through each pull rod is uniform and through the longitudinal centerline of the specimen so as to obviate the introduction of bending stresses in the specimen during testing.

Other and further objects of the present invention will become obvious upon an understanding of the illustrative embodiment about to be described or will be indicated in the appended claims, and various advantages not referred to herein will occur to one skilled in the art upon employment of the invention in practice.

Inasmuch as the self aligning-multiple hydraulic piston, load-applying mechanism described in the aforementioned patent is preferably used in conjunction with the pull rod specimen gripping apparatus of the present invention for the purpose of tensile testing dogbone-shaped, plate-type tensile specimens, the aforementioned patent is incorporated herein by reference.

A preferred embodiment of the invention has been chosen for the purpose of illustration and description. The preferred embodiment illustrated is not intended to be exhaustive nor to limit the invention to the precise form shown. The preferred embodiment is chosen and described in order to best explain the principles of the invention and their application and practical use to thereby enable others skilled in the art to best utilize the invention in various embodiments and modifications as are best adapted to the particular use contemplated.

DETAILED DESCRIPTION OF THE INVENTION

The present invention as briefly described above is directed to apparatus used for determining strength characteristics of various structural materials especially ceramics by dynamic fatigue testing of dogbone-shaped, flat or plate-type tensile specimens. In accordance with the present invention, a pull rod assembly is used in conjunction with the force applying mechanism for gripping opposite sides of the dogbone-shaped specimens in such a manner that the tension loading on the specimen applied via the pull rod assembly is always through the longitudinal axis or centerline of the specimen so as to assure that undesirable bending stresses will not be imposed upon the specimen during the application of the tension loading. This specimen gripping pull rod assembly of the present invention, as will be described in greater detail below, is self-aligning so as to be usable with tensile specimens in which the shoulders on each of the T-shaped ends of the dogbone-shaped tensile specimens are not in the same or common horizontal or transverse plane so as to minimize or obviate the strict or close machining requirements heretofore required for preparing dogbone-shaped ceramic specimens used in tensile testing.

In accordance with the present invention, a pull rod assembly is disposed at each longitudinal end of the dogbone-shaped, plate-type specimen with each pull rod assembly gripping and end section of the specimen so that the applied force is directed along the longitudinal axis of the specimen. This applied force on the specimen may be provided by displacing each of the pull rod assemblies in opposite directions along a common centerline or by fixedly securing one of the pull rod assemblies and applying a dynamic load to the other pull rod assembly for dynamically testing the tensile specimen. The pull rod assemblies are each supported by a suitable mechanism which is capable of displacing the pull rod assemblies in opposite directions for applying the tensile loading through the centerline of the specimen. Preferably, this displacement of each pull rod assembly is achieved by using the tensile applying mechanism as described in the aforementioned U.S. patent in which a plurality of hydraulic pistons are used for tensile loading the ceramic specimen during tensile testing while applying little or no bending stresses to the specimen.

Figure 1:
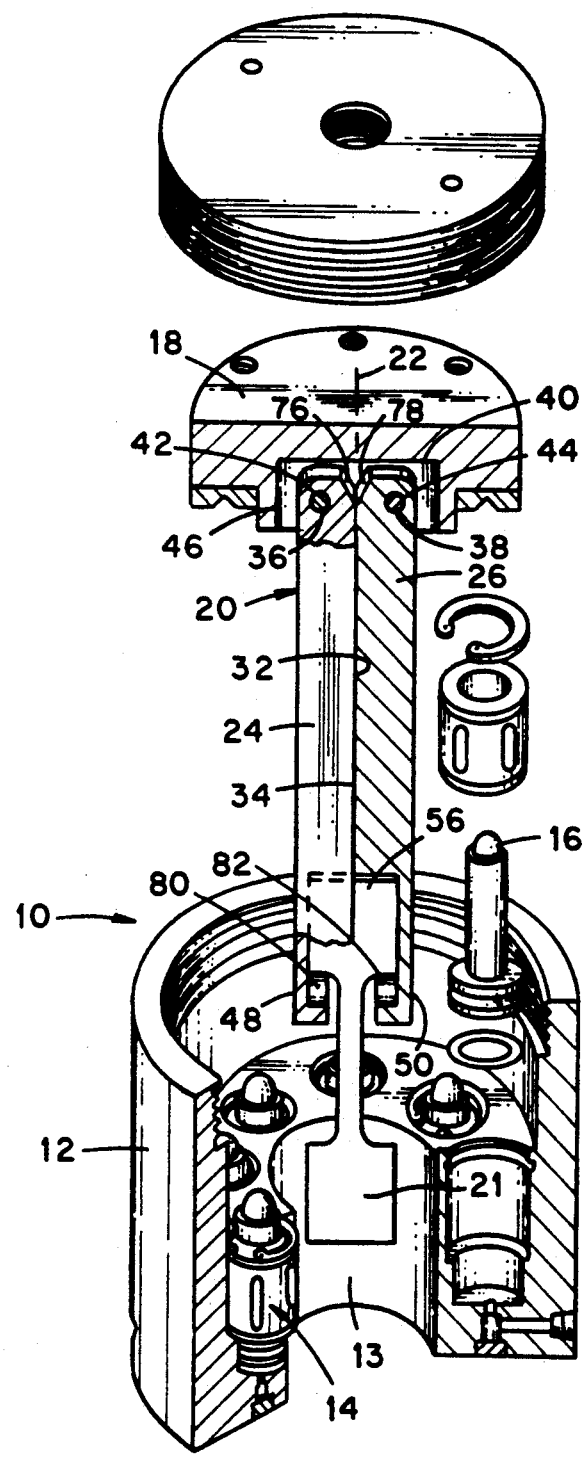
FIG. 1 is a vertical sectional view illustrating the self-aligning multiple hydraulic piston load applying mechanism with the self-aligning specimen gripping apparatus of the present invention as used for tensile testing a dogbone-shaped, plate-type tensile specimen.

Generally, as shown in FIG. 1 and specifically described in the aforementioned U.S. patent, the tension applying mechanism 10 employing multiple hydraulic pistons comprises an annular housing 12 having an elongated central cavity 13 and supporting a plurality of hydraulic piston-cylinder assemblies 14 circumferentially spaced on an annular shelf placed within the cavity 13 with one end of each piston 16 bearing against surfaces of a V-shaped groove 17 in a peripheral region of a movable disk-shaped flange or plate 18 disposed at one end of the cavity 13 and supporting the specimen pull rod assembly 20. The plate 18 and the pull rod assembly 20 attached thereto are displaced within the housing cavity 13 by conveying hydraulic fluid to each piston assembly 14 at the same pressure so that the pistons 16 will exert a uniform force upon the plate 18 with the resulting applied force acting on the tensile specimen 21 being in alignment with the longitudinal centerline 22 of the pull rod assembly 20 and the specimen 21 at the center of the plate 18. The dogbone-shaped, plate-type specimen gripping fixture or assembly 20 of the present invention replaces the pull rod arrangement described in the aforementioned patent that is used solely for the gripping of cylindrical specimens.

Figure 2:
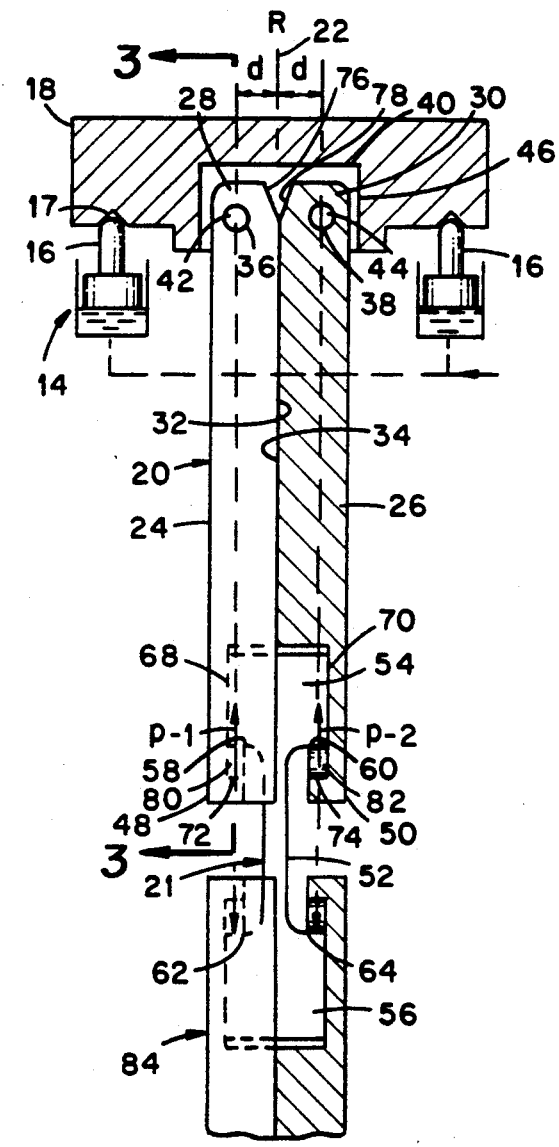
FIG. 2 is a vertical sectional view, partly broken away, illustrating further details of the specimen gripping apparatus of the present invention.
Figure 3:
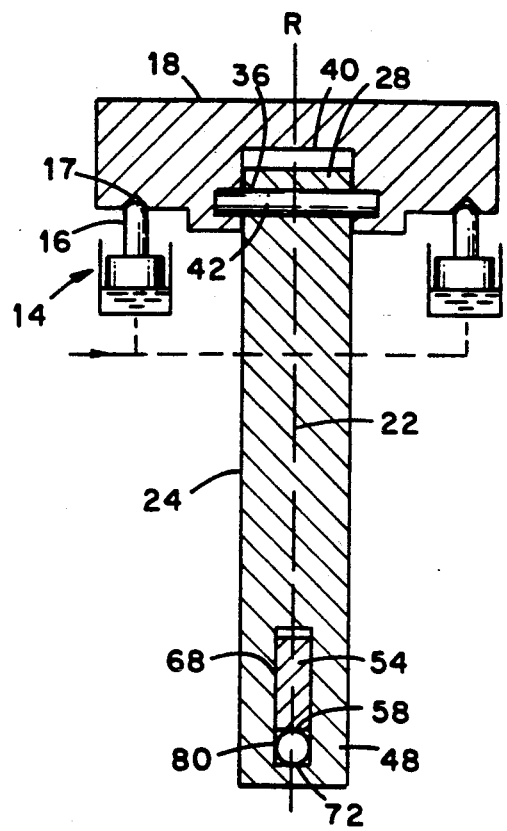
FIG. 3 is a vertical sectional view taken along lines 3—3 of FIG. 2 for showing more details of the specimen gripping apparatus of the present invention.

As shown in FIGS. 1-3, the pull rod assembly 20 comprises of a pair of elongated generally rectangularly shaped pull rods 24 and 26, of a uniform length sufficient to extend through the cavity 13 of the housing 12 of the load applying system 10. End regions 28 and 30 of the pull rods 24 and 26 are attached to the central region of the plate 18 so that the pull rods 24 and 26 extend from the plate 18 in a side-by-side relationship with a flat side 32 of pull rod 24 in an abutting relationship with a flat side 34 of pull rod 26 over essentially the entire length thereof. The pull rods 24 and 26 are attached to the plate 18 by providing the end regions 28 and 30 with throughgoing passageways or bores 36 and 38 respectively with these bores being disposed parallel to one another in the same horizontal plane and perpendicular to the longitudinal axis of the pull rods 24 and 26 when they are attached to the end cap 18. As shown in FIGS. 1-3, the end regions 28 and 30 of the pull rods 24 and 26 extend into a receptacle 40 at the center of the end cap and are held in place by horizontally extending pins 42 and 44 which are supported at the ends thereof by the walls 46 of the receptacle 40. When so mounted, the unattached or free end regions 48 and 50 of pull rods 24 and 26 can be displaced in opposite generally transverse directions by pivoting the pull rods 24 and 26 about the pins 42 and 44 in order to insert the dogbone-shaped, plate-type specimen 21 between the pull rods 24 and 26. Also, the pins 42 and 44 permit the pull rods 24 and 26 to be longitudinally positioned with respect to each other during the application of a tensile load on a dogbone-shaped tensile specimen 21 when the shoulders on either end thereof are not in a common horizontal plane. This longitudinal positioning of the pull rods 24 and 26 is achieved by a slight tipping of the plate 18 in a horizontal plane as caused by the multiple piston assemblies 14 seeking to apply a uniform load on the plate 18 with such tipping of the plate 18 continuing until the pull rods 24 and 26 are sufficiently longitudinally positioned with respect to one another so as to bear similar loads. The longitudinal axes of pins 42 and 44 are disposed in the same plane as the point of contact between the ends of the pistons 16 and the V-shaped groove 17 in plate 18. This alignment of the longitudinal axes of the pins 42 and 44 with the ends of the pistons 16 is important to the operation of the pull rod assembly 20. In the event this alignment is not provided, tilting of the plate 18 during the application of the load on the tensile specimen 21 may displace the resulting force away from the center of the plate 18 so as to apply an unequal loading on the tensile specimen 21.

The tensile specimen 21 generally comprises an elongated plate with a central testing or working section 52 and generally T-shaped end sections 54 and 56 provided with shoulders 58 and 60 on opposite sides of end section 54 and shoulders 62 and 64 on opposite sides of end section 56. These shoulders 58, 60, 62, and 64 extend generally perpendicular to the longitudinal centerline 22 of the specimen 21 and are preferably provided so that each pair of shoulders 58 and 60 and shoulders 62 and 64 are in a common horizontal plane. However, with the present invention these shoulders need not be in the same horizontal plane in order to provide accurate tensile testing of the specimens due to the self-aligning features of the pull rod assembly 20, thus considerably reducing the cost of preparing tensile specimen to precise tolerances.

In order to support the tensile specimen 21 by the pull rods 24 and 26, the unattached or free-end regions 48 and 50 of the pull rods 24 and 26 are provided with vertically extending recesses 68 and 70 of generally rectangular configurations. These recesses 68 and 70 defined by wall regions in each pull rod are in the facing sides 32 and 34 of the pull rods 24 and 26 and are located in common vertical and horizontal orientations so as to face one another when the pull rods are in a side-by-side relationship with the lower wall segment 72 of the recess 68 being in essentially the same horizontal plane as the lower wall segment 74 of the recess 70. The size of the recesses 68 and 70 is such that the width and length of the recesses is sufficiently greater than that of the T-shaped end sections 54 and 56 of the specimen 21 so as to readily receive the end section 54 or 56 of the specimen therein. The attaching of the T-shaped end section 54 or 56 to the pull rods 24 and 26 is provided by separating the pull rods at the lower end regions 48 and 50 thereof through the pivoting of the rods 24 and 26 about the pins 42 and 44 a sufficient distance for permitting the insertion of the T-shaped end section 54 of the tensile specimen 21 into the recesses 68 and 70 as shown in FIGS. 1-3. To facilitate this pivoting or separation of the end regions 48 and 50 of the pull rods 24 and 26, the upper ends of the facing pull rod surfaces 32 and 34 are provided with notches 76 and 78.

With the end section 54 of the tensile specimen in the recesses 68 and 70 or prior thereto, cylindrical rollers or solid cylinders 80 and 82 are placed in the base of each recess 68 and 70 so as to be located between the recess walls 72 and 74 and the shoulders 58 and 60 of the specimen, thus supporting the shoulders of the end section 54 of the tensile specimen 21 on the rollers 80 and 82. The cylindrical rollers 80 and 82 are of a length generally corresponding to the depth of the recesses 68 and 70 and of a diameter generally corresponding to the width of the recesses 68 and 70. This depth of the recesses 68 and 70 is slightly less than the length of the side sections of the T-shaped end sections 54 or 56 of the tensile specimen 21. The axes of these rollers 80 and 82 are aligned with the mid-plane or centerline 22 of the specimen so that the supporting forces pass through the mid-plane of the specimen 21 without introducing bending stresses in the working section of the specimen 21.

As best shown in FIGS. 2 and 3, the pins 42 and 44 are provided through the ends of the pull rods 24 and 26 at locations which are equally spaced from the center of the plate 18 and the centerline 22 of the specimen supporting assembly as defined by the interface between the pull rods 24 and 26. This distance "d" is such that the pins 42 and 44 are in longitudinal alignment with the midpoint of the rollers 80 and 82 so as to assure that any force applied through the pins 42 and 44 is in the same longitudinal plane as that of the load bearing rollers 80 and 82 and thereby minimizing or eliminating any bending stresses from being introduced into the specimen 21 during the longitudinal displacement of the pull rods 24 and 26 by the movement of the plate 18.

In order to uniformly distribute the tensile loads applied to the specimen 21 by the displacement of each of the pull rods 24 and 26 through the movement of the plate 18 provided by the pistons 16, the tensile loads as generally shown at p-1 and p-2 are evenly distributed on the working section 52 of the specimen so that the resultant forces "R" applied to the specimen will pass through the centerline 22 of the specimen 21. The testing of the specimen 21 under a pure tension loading requires that the forces, p-1 and p-2, be equal in magnitude and act symmetrically with respect to the centerline 22 of the specimen. With the pins 42 and 44 extending through the pull rods 24 and 26 being equally spaced apart from one another with respect to the center of the plate 18 and the centerline 22 of the pull rod assembly 20 and the specimen 21, the dynamic forces acting on the specimen 21 through the side-by-side pull rods 24 and 26 is equally divided between each pin 40 and 42 as provided by the tipping of the plate 18 by the piston assemblies 14. Thus, if the flat shoulders 58 and 60 at one end of the plate-type specimen 21 are in the same horizontal plane then the plate 18 will remain level and perpendicular to the pull rods 24 and 26 during the application of tension on the tensile specimen 21. However, in the event shoulder 58 is higher or lower then shoulder 60, the pull rods 24 and 26 must move up or down relative to one another by the tipping of the plate 18 and the pivoting about pins 42 and 44 in order to maintain the tensile force acting through the longitudinal centerline 22 of the pull rod assembly 20 and the specimen 21. Thus, by the self adjusting action of the pull rods 24 and 26 during the application of the tensile loading on the specimen 21 having shoulders in different horizontal planes, provides for tensile loads to be applied to the specimen 21 without introducing bending stresses in the specimen.

The T-shaped end section 56 of the tensile specimen 21 is similarly mounted in the pull rod system generally shown at 84 and formed of a construction similar to that of pull rod assembly 20 described above.

It will be seen that the present invention provides an improved mechanism for tensile testing of ceramic specimens of dogbone-shaped, plate-type configurations wherein the tensile loading of the specimens is applied in such a manner that bending forces are not introduced into the specimen so as to disrupt the accuracy in the tensile test. Further, the pull rod arrangement of the present invention facilitates the testing of specimens that have been prepared by using less than the precise machining practices that were heretofore required for accurately testing tensile specimens since the self-adjusting pull rod system of the present invention will readily and automatically compensate for specimens having shoulders in different horizontal planes.

What is claimed is:

1. Apparatus for gripping a plate-type tensile specimen having generally T-shaped end regions in a dynamic tension fatigue testing apparatus comprising an annular housing having an open-ended elongated cavity therein, a plurality of hydraulic piston means supported by the housing in a spaced array about the cavity, and a specimen-supporting plate means overlying the piston means at one end of the elongated cavity and displaceable by said piston means in a longitudinal direction with respect to the longitudinal axis of the cavity, said apparatus for gripping a flat plate-type tensile specimen comprising:

a pair of elongated pull rods each having oppositely disposed first and second end regions;

a pair of mounting means carried by said plate means with each mounting means for pivotally attaching the first end region of each of said pull rods in a central region of said plate means for supporting said pair of elongated pull rods in a side-by-side relationship along a common longitudinal centerline within said cavity;

recess means in the second end region of each of said pull rods in adjacently disposed surface regions thereof with said recess means facing one another and each adapted to receive one side of one of the generally T-shaped end regions of the plate-type tensile specimen; and load-bearing means positionable in each of said recess means and adapted to bear against a shoulder on each side of the generally T-shaped end region of the plate-type tensile specimen when a tensile loading is applied thereon.

2. Apparatus for gripping a plate-type tensile specimen as claimed in claim 1, wherein each of said pull rods is of a generally rectangular configuration, wherein said pull rods have side surfaces thereon disposed in a substantially abutting relationship over substantially the full length of the pull rods, and wherein the common longitudinal centerline of the pull rods is defined by the interface between said side surfaces.

3. Apparatus for gripping a plate-type tensile specimen as claimed in claim 1, wherein the first end region of each pull rod is provided with a throughgoing bore, wherein the bores in the pull rods are disposed parallel to one another in a common plane transverse to both the longitudinal axis of the tensile specimen when received in said recess means and to the common longitudinal centerline of the pull rods, and wherein each of said mounting means is provided by pin means extending through the bore in each of the pull rods for pivotally attaching each of the pull rods to the plate means and thereby permitting the pull rods to be displaced relative to one another along the common longitudinal centerline for applying a substantially uniform tensile load to each side of the generally T-shaped end region of the tensile specimen during the application of the tensile loading.

4. Apparatus for gripping a plate-type tensile specimen as claimed in claim 3, wherein each of said recess means is of a generally rectangular configuration and defined by wall means with a segment thereof disposed at a location nearest to an end of each pull rod remote to said mounting means, and wherein each of said load-bearing means is positioned in each recess means at a location intermediate said segment of the wall means and a shoulder on a side of the T-shaped end region of the plate-type tensite specimen.

5. Apparatus for gripping a plate-type tensile specimen as claimed in claim 4, wherein the pin means and the load-bearing means of each pull rod are uniformly spaced from the common longitudinal centerline of the pull rods.

6. Apparatus for gripping a plate-type tensile specimen as claimed in claim 3, wherein each of said load-bearing means is provided by a solid cylinder, wherein each solid cylinder is of a length substantially corresponding to the depth of the recess means, and wherein each solid cylinder is of a diameter substantially corresponding to the width of the recess means.

7. Apparatus for gripping a plate-type tensile specimen as claimed in claim 3, wherein the second end regions of the pull rods are pivotable in opposing directions generally transverse to the common longitudinal centerline of the pull rods for sufficiently exposing each of the recess means for inserting the sides of generally T-shaped end section of the tensile specimen into the recess means.

8. Apparatus for gripping a plate-type tensile specimen as claimed in claim 3, wherein the tipping of the plate means in a plane generally transverse to the common longitudinal centerline of the pull rods provides for the relative displacement of the pull rod means with this tipping of the plate means being terminated when the tensile loading is divided essentially equally between said pair of mounting means.

9. Apparatus for gripping a plate-type tensile specimen as claimed in claim 3, wherein the plate means is provided with a receptacle in the central region thereof, and wherein said first end regions of both of the pull rods are positioned in the receptacle with the center of the plate means in axial alignment with the common longitudinal centerline of the pull rods.

* * * * *